US009592265B2

(12) United States Patent
Kappagoda et al.

(10) Patent No.: US 9,592,265 B2
(45) Date of Patent: Mar. 14, 2017

(54) MODULATION OF OXIDATIVE STRESS, INFLAMMATION, AND IMPAIRED INSULIN SENSITIVITY WITH GRAPE SEED EXTRACT

(71) Applicant: THE REGENTS OF THE UNIVERSITY OF CALIFORNIA, Oakland, CA (US)

(72) Inventors: Chulani T. Kappagoda, Sacramento, CA (US); Britt Burton-Freeman, Lisle, IL (US); Indika Edirisinghe, Oak Lawn, IL (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/391,893

(22) PCT Filed: Apr. 10, 2013

(86) PCT No.: PCT/US2013/035944
§ 371 (c)(1),
(2) Date: Oct. 10, 2014

(87) PCT Pub. No.: WO2013/155166
PCT Pub. Date: Oct. 17, 2013

(65) Prior Publication Data
US 2015/0328274 A1 Nov. 19, 2015

Related U.S. Application Data

(63) Continuation-in-part of application No. 13/841,673, filed on Mar. 15, 2013.

(60) Provisional application No. 61/622,339, filed on Apr. 10, 2012.

(51) Int. Cl.
| A61K 36/00 | (2006.01) |
| A61K 36/87 | (2006.01) |
| A61K 31/353 | (2006.01) |
| A61K 31/192 | (2006.01) |

(52) U.S. Cl.
CPC ............ *A61K 36/87* (2013.01); *A61K 31/192* (2013.01); *A61K 31/353* (2013.01)

(58) Field of Classification Search
None
See application file for complete search history.

(56) References Cited

U.S. PATENT DOCUMENTS 6,544,581 B1 * 4/2003 Shrikhande ........... A23L 1/2751
426/425
2007/0071841 A1 * 3/2007 Kappagoda .................. 424/766

FOREIGN PATENT DOCUMENTS

SU    1533633 A1    1/1990

OTHER PUBLICATIONS

Doustar et al, Study of grape seed extract on experimental diabetic nephropathy in rat. IUBMB Life, (2009) vol. 61, No. 3, pp. 312. Abstract No: S12-27.*
Blanco-Colio, L.M. et al., "Red Wine Intake Prevents Nuclear Factor-κB Activation in Peripheral Blood Mononuclear Cells of Healthy Volunteers During Postprandial Lipemia"; Circulation (2000); vol. 102; pp. 1020-1026.
Brasnyó, P. et al., "Resveratrol Improves Insulin Sensitivity, Reduces Oxidative Stress and Activates the Akt Pathway in Type 2 Diabetic Patients"; Br. J. Nutr. (2011); vol. 106; pp. 383-389.
Burton-Freeman, B., et al., "Protective activity of processed tomato products on postprandial oxidation and inflammation: A clinical trial in health weigh men and women"; Mol. Nutr. Food Res. (2012); vol. 56; pp. 622-631.
Burton-Freeman, B. et al., "Strawberry Modulates LDL Oxidation and Postprandial Lipemia in Response to High-Fat Meal in Overweight Hyperlipidemic Men and Women"; J. Am. Col. Nutr. (2010); vol. 29:1; pp. 46-501.
Chis, I.C. et al., "Antioxidant effects of a grape seed extract in a rat model of diabetes mellitus"; Diab. Vasc. Dis. Res. (2009); vol. 6:3, pp. 200-204.
Edirisinghe, I. et al., "Strawberry anthocyanin and its association with postprandial inflammation and insulin"; Br. J. Nutr. (2011); vol. 106; pp. 913-922.
Kim, Y. et al., "Antioxidant and Cytoprotective Effects of Oligomeric and Polymeric Procyanidin Fractions from Deffated Grape Seed in PC12 Cells"; J. Med. Food. (2012); vol. 15:5; pp. 490-494.
Leifert, W. R., et al., "Cardioprotective Actions of Grape Polyphenols" Nutr. Res. (2008); vol. 28; pp. 729-737.
Leighton, F., et al., "Plasma Polyphenols and Antioxidants, Oxidative DNA Damage and Endothelial Function in a Diet and Wine Intervention Study in Humans"; Drugs Exp. Clin. Res. (1999); vol. 25(2-3); pp. 133-141.
Meeprom, A. et al., "Grape Seed Extract Supplementation Prevents High-Fructose Diet-Induced Insulin Resistance in Rats by Improving Insulin and Adiponectin Signaling Pathways"; Br. J. Nutr. (2011); vol. 106:8; pp. 1173-1181.
Neri, S. et al., "Effects of Antioxidant Supplemental on Postprandial Oxidative Stress and Endothelial Dysfunction: A Single-Blind, 15-Day Clinical Trial in Patients with Untreated Type 2 Diabetes, Subjects with Impaired Glucose Tolerance, and Healthy Controls"; Clin. Ther. (2005); vol. 27:11; pp. 1764-1173).
Perez-Herrera, A., et al., "The Postprandial Inflammatory Response after Ingestion of Heated Oils in Obese Persons is Reduced by the Presence of Phenol Compounds"; Mol. Nutr. Food Res. (2012), vol. 56; pp. 510-514.

(Continued)

*Primary Examiner* — Qiuwen Mi
(74) *Attorney, Agent, or Firm* — Andrews Kurth Kenyon LLP (57) ABSTRACT

Method for modulating oxidative stress, inflammation, and impaired insulin sensitivity in a subject by using a grape seed extract, the method being useful in modulating postprandial oxidative stress, inflammation, and impaired insulin sensitivity in patients suffering from Metabolic Syndrome (MetS). The method comprising administering a therapeutically effective amount of a grape seed extract and a pharmaceutically acceptable excipient. The grape seed extract is a polyphenolic extract comprising proanthocyanidins and anthocyanidins.

12 Claims, 4 Drawing Sheets

(56) References Cited

OTHER PUBLICATIONS

Prior, R.L. et al., "Plasma Antioxidant Captivity Changes Following a Meal as a Measure of the Ability of a Food to Alter In Vivo Antioxidant Status"; J. Am. Coll. Nutr. (2007); vol. 26:2; pp. 170-181.

Prior, R.L. et al., "Occurrence and biological significance of proanthocyanidins in the American diet"; Phytochemistry (2005); vol. 66; pp. 2264-2280.

Rahman, I. et al., "Regulation of Inflammation and Redox Signaling by Dietary Polyphenols"; Biochem. Pharmacol. (2006); vol. 72; pp. 1439-1452.

Rahman, I, "Dietary Polyphenols Mediated Regulation of Oxidative Stress and Chromatin Remodeling in inflammation"; Nutr. Rev. (2008); vol. 66:Suppl 1; pp. S42-S45.

Sandhya, K. et al., "Strawberry Extract Attenuates Oxidative Stress-Induced Impaired Insulin Signaling in vitro in Human Skeletal Muscle Cells"; The FASEB Journal (2010); Abstract 24/1; pp. 541.13. http://www.fasebj.org/cgi/content/meeting.

Serafini, M. et al., "Alcohol-Free Red Wine Enhances Plasma Antioxidant Capacity in Humans"; J Nutr. (1998); vol. 128; pp. 1003-1007.

Singleton, V.L. et al., "Analysis of total phenols and other oxidation substrates and antioxidants by means of Folin-Ciocalteu Reagent"; Methods in Enzymology (1999); vo. 299; pp. 152-178.

Sivaprakasapillai., B. et al., "Effect of Grape Seed Extract on Blood Pressure in Subjects with the Metabolic Syndrome"; Meta. Clin. Exper. (2009); vol. 58; pp. 1743-1746.

Stull, A.J. et al., "Bioactives in Blueberries Improve Insulin Sensitivity in Obese, Insulin-Resistant Men and Women"; J. Nutr. (2010); vol. 140; pp. 1764-1768.

Waterhouse, A.L., "Determination of Total Phenolics", in Current Protocols in Food Analytical Chemistry, pp. I1.1.1-I1.1.8; John Wiley & Sons (2002).

Burton-Freeman, B. "Postprandial metabolic events and fruit-derived phenolics: a review of the science", Br. Journal of Nutrition (2010), vol. 104, pp. S1-S14.

GRAS Notice 000093 Summary of Data for Chemical Selection (Polyphenolics, Inc. Jan. 16, 2013), 100 pgs. retrived on May 17, 2013 from www.accessdata.fda.gov.

International Search Report dated Jul. 23, 2013 from PCT/US2013/035944.

Edirisinghe, I. et al., "Grape Seed Extract Modifies Insulin Resistance Induced by a High Fat/Carbohydrate Meal in Metabolic Syndrome Patients", FASEB, J. (2010); vol. 24; (Abstract only).

Edirisinghe, I. et al., "Grape Seed Extract Modifies Insulin Resistance Induced by a High Fat/Carbohydrate Meal in Metabolic Syndrome Patients", FASEB, J. (2012); vol. 26; (Abstract only).

Tadapaneni, R. K. et al., "Grape Seed Extract Attenuates Oxidative Stress Induced by High Fat/Carbohydrate Meal in Metabolic Syndrome Patients", FASEB, J. (2010); vol. 24 (Abstract only).

Tadapaneni, R. K. et al., "Grape Seed Extract Attenuates Oxidative Stress Induced by High Fat/Carbohydrate Meal in Metabolic Syndrome Patients", FASEB, J. (2012); vol. 26 (Abstract only).

Kar, P., et al. "Effects of Grape Seed Extract in Type 2 Diabetic Subjects at High Cardiovascular risk: A Double Blind Randomized Placebo Controlled Trial Examining Metabolic Markers, Vascular Tone, Inflammation, Oxidative Stress and Insulin Sensitivity", Diabetic Medicine (2009); vol. 26:5, pp. 526-531.

Suwannaphet, W. et al. "Preventive Effect of Grape Seed Extract Against High-Fructose Diet-Induced Insulin Resistance and Oxidative Stress in Rates", Food and Chemical Toxicology (2010); vol. 48, pp. 1853-1857.

Baiges, I. et al. "Lipogenesis is Decreased by Grape Seed Proteomics of Rats Fed a High Fat Diet", Molecular & Cellular Proteomics (2010), vol. 9:7, pp. 1499-1513.

Rosenberg, D.E., "Insulin Resistance, Diabetes and Cardiovascular Risk: Approaches to Treatment", Diabetes, Obesity and Metabolism (2005); vol. 7; pp. 642-653.

Supplementary Search Report, dated Sep. 15, 2015, from related EP Application No. 13 77 6017.

\* cited by examiner

MODULATION OF OXIDATIVE STRESS, INFLAMMATION, AND IMPAIRED INSULIN SENSITIVITY WITH GRAPE SEED EXTRACT

CROSS REFERENCE TO RELATED APPLICATIONS

This application is a U.S. national phase of international application, PCT/US2013/035944, filed Apr. 10, 2013, which claims the priority of U.S. application No. 61/622,339 filed Apr. 10, 2012 and Ser. No. 13/841,673 filed Mar. 15, 2013, the disclosures of which patent applications are incorporated by reference herein.

FIELD OF THE INVENTION

The invention relates to the use of grape seed extracts in modulating oxidative stress, inflammation, and impaired insulin sensitivity in a patient, particular a patient suffering from metabolic syndrome.

BACKGROUND OF THE INVENTION

Metabolic syndrome (Met.S) is a growing medical problem in industrialized countries and is diagnosed when three of the following factors are present: abdominal obesity, elevated serum triglycerides, low serum high density lipoprotein (HDL) concentration, elevated blood pressure, and elevated blood glucose. The syndrome is associated with insulin-resistance, impaired glucose control, atherogenic dyslipidemia, oxidative stress, and enhanced cardiovascular risk.

Insulin resistance, a characteristic feature of metabolic syndrome (MetS), is known to be associated with impaired glucose tolerance and impaired fasting glucose. Consumption of a meal that is high in readily available carbohydrates and fat causes postprandial increases in glycemia and lipidemia and markers of oxidative stress, inflammation and insulin resistance.

Hyperglycemia has been shown to impose cellular oxidative stress through the increased generation of endogenous reactive oxygen species (ROS) particularly in adipose tissue, both in vitro and in vivo. Increased ROS, in turn promotes inflammation by activating nuclear factor-kappaB (NF-κB) transcription complex resulting in the expression of a number of genes coding for pro-inflammatory cytokines.

Oxidative stress and inflammation are believed to play a critical role in the pathogenesis of several diseases including atherosclerosis and diabetes. Oxidative stress impairs glucose uptake in muscle and fat and decreases insulin secretion from β cells of the pancreas, resulting in prolonged hyperglycemia, increased glycation endproducts and endothelial dysfunction, all of which contribute to the development of atherosclerosis. Since insulin resistance presents before the development of diabetes, early intervention strategies designed to reduce insulin resistance and improve glucose control could ameliorate unfavorable effects on blood vessels and risk for micro- and macro-vascular disease. One possible approach for decreasing insulin resistance and improving glucose control is to enhance the anti-oxidant status of the body.

As described previously consumption of a meal that is high in readily available carbohydrates and fat results in a postprandial increase in markers of oxidative stress, inflammation and insulin resistance (See, Burton-Freeman et al. I, (Burton-Freeman B, Talbot J, Park E, Krishnankutty S, Edirisinghe I., Mol Nutr Food Res. 2012 Feb. 14. doi: 10.1002/mnfr.201100649. [Epub ahead of print] PubMed PMID: 22331646); Burton-Freeman et al. II, (Burton-Freeman B, Linares A, Hyson D, Kappagoda T., J Am Coll Nutr. 2010 February; 29(1):46-54); and Edirisinghe et al., (Edirisinghe I, Banaszewski K, Cappozzo J, Sandhya K, Ellis C L, Tadapaneni R, Kappagoda C T, Burton-Freeman B M., Br J Nutr. 2011 September; 106(6):913-22).). These changes are accentuated in states where insulin function is impaired such as in MetS (REF). It has been suggested that fruits and vegetables, particularly those with a higher polyphenolic content, have favorable effects on human health due to their ability to modulate oxidative and inflammatory stress in peripheral tissues (See, Rahman I., Nutr Rev. 2008 August; 66 Suppl 1:S42-5; and Rahman I, Biswas S K, Kirkham P A, Biochem Pharmacol. 2006 Nov. 30; 72(11):1439-52.). Grape seeds are a concentrated source of polyphenols and have received considerable attention for their antioxidant capacity and biological effects (See, Leifert W R, Abeywardena M Y, Nutr Res 2008; 28:729-37; Chis I C, Ungureanu M I, Marton A, Simedrea R, Muresan A, Postescu I D, Decea N., Diab Vasc Dis Res. 2009 July; 6(3):200-4; Meeprom A, Sompong W, Suwannaphet W, Yibchok-anun S, Adisakwattana S., Br J Nutr. 2011 October; 106(8):1173-81; and Kim Y, Choi Y, Ham H, Jeong H S, Lee J., J Med Food. 2012 Mar. 8. [Epub ahead of print] PubMed PMID: 22400909.).

There is a need for a method of modulating the oxidative stress, inflammation, and impaired insulin sensitivity in patients with metabolic syndrome (Met.S). Herein is provided a method comprising acute supplementation with grape seed extract (GSE) in the diet of a patient suffering from Met.S to improve antioxidant status and impaired insulin action following consumption of a pro-oxidative high carbohydrate, moderate fat meal.

SUMMARY OF THE INVENTION

In one embodiment, the present invention provides a method of modulating oxidative stress, inflammation, impaired insulin sensitivity or a combination thereof in a subject, comprising administering to the subject a therapeutically effective amount of a grape seed extract.

In another embodiment, the present invention provides a pharmaceutical composition comprising a grape seed extract and a pharmaceutical acceptable excipient for modulating post-prandial oxidative stress, inflammation, impaired insulin sensitivity, or a combination thereof in a subject suffering from Metabolic Syndrome.

In another embodiment, the present invention provides a method of treating a subject suffering from Metabolic Syndrome comprising administering to the subject a therapeutically effective amount of a grape seed extract. Such method can be used in treating postprandial oxidative stress, inflammation, impaired insulin sensitivity or a combination thereof in a subject suffering from Metabolic Syndrome. Such method may also comprise treating or preventing type II diabetes in a subject in a pre-diabetic condition and suffering from Metabolic Syndrome.

In another embodiment there is provided for a use of a therapeutically effective amount of a grape seed extract for modulating oxidative stress, inflammation, impaired insulin sensitivity or a combination thereof in a subject.

In another embodiment there is provided for a use of a grape seed extract for the preparation of a medicament for treating or preventing Metabolic Syndrome.

In another embodiment there is provided for a use of a grape seed extract for the preparation of a medicament for treating or preventing type II diabetes in a subject in a pre-diabetic condition and suffering from Metabolic Syndrome.

BRIEF DESCRIPTION OF THE FIGURES

FIG. 1: Illustrates Postprandial plasma Oxygen Radical Absorbance Capacity (ORAC) values. (A) Hydrophilic ORAC values and (B) lipophilic ORAC values. Values represent mean plasma ORAC values with their standard errors by vertical bars at respective time points before and after a high fat-carbohydrate breakfast meal with the grape seed extract (GSE) or the placebo. Post prandial ORAC values in the hydrophilic phase as assessed by positive incremental area under the curve was significantly increased after the meal with the GSE compared with the placebo (**P<0.01, n=12).

FIG. 2: Illustrates Postprandial plasma oxidized LDL (OxLDL) concentrations. Values represent mean plasma Ox-LDL concentrations with their standard errors by vertical bars at respective time points before and after a high fat-carbohydrate breakfast meal with the grape seed extract (GSE) or the placebo. Post prandial OxLDL concentrations at 5 hr time point is significantly decreased in GSE compared with the placebo (**P<0.01, n=12).

FIG. 3: Illustrates Postprandial plasma inflammatory markers. (A): Interlukin-6 (IL-6) (B): Tumor necrotic factor-α (TNF-α). Values represent mean plasma IL-6 or TNF-α concentrations with their standard errors by vertical bars at respective time points before and after a high-fat-carbohydrate breakfast meal with the grape seed extract (GSE) or the placebo. Postprandial plasma IL-6 or TNF-α concentrations as assessed by positive area under the curve were not significantly different after the meal with the GSE compared with the placebo (P>0.05, n=12).

FIG. 4: Illustrates Postprandial plasma glucose concentrations. Values represent mean plasma glucose concentrations with their standard errors by vertical bars at respective time points before and after a high fat-carbohydrate breakfast meal with the grape seed extract (GSE) or the placebo. Postprandial glucose concentrations as assessed by total area under the curve was significantly lower after the meal with the GSE compared with the placebo (* P<0.05, n=12).

FIG. 5: Illustrates Postprandial plasma insulin concentrations. Values represent mean plasma insulin concentrations with their standard errors by vertical bars at respective time points before and after a high fat-carbohydrate breakfast meal with the grape seed extract (GSE) or the placebo. Postprandial glucose concentrations as assessed by total area under the curve was not significantly different after the meal with the GSE compared with the placebo (P>0.05, n=12).

DETAILED DESCRIPTION

Herein is provided a method comprising acute supplementation with grape seed extract (GSE) in the diet of a patient suffering from Met.S to improve antioxidant status and impaired insulin action following consumption of a pro-oxidative high carbohydrate, moderate fat meal. In one embodiment is provided a method of modulating oxidative stress, inflammation, and impaired insulin sensitivity in a subject, comprising administering to the subject a therapeutically effective amount of a grape seed extract (GSE). Also is provided a method of treating a subject suffering from Metabolic Syndrome comprising administering to the subject a therapeutically effective amount of a grape seed extract. Such method can be used in treating postprandial oxidative stress, inflammation, impaired insulin sensitivity or a combination thereof in a subject suffering from Metabolic Syndrome. Such method may also comprise treating or preventing type II diabetes in a subject in a pre-diabetic condition and suffering from Metabolic Syndrome.

As described herein a high fat content meal is considered a meal of which 40% or more of the calories is derived from fat. A high fat content diet therefore is considered a diet by which the daily 40% or more of the calorie intake is from fat. A moderate fat content meal or daily diet is considered one wherein 30% to 40% of the calories is derived from fat. A normal fat content meal or daily diet is one wherein 25% to 30% of the calories are derived from fat.

As used herein the term "subject" refers to a human, who is 18 years of age or older and/or having a body mass index of 18.5 and above, for example, between 18.5 and 40 kg/m². The term "bioavailability" as used herein refers to the rate and extent to which the active ingredient or active moiety is absorbed from a drug product and becomes available at the site of action. The bioavailability of a pharmaceutical composition can be determined, for example, by any pharmacokinetic parameter known to the person skilled in the art. Examples of such parameters include: $t_{1/2}$ (half-life), $C_{min}$ (minimal plasma concentration), $C_{max}$ (maximal plasma concentration), and AUC (area under the curve). The AUC may be for example, the area under the plasma/serum/blood concentration-time curve. AUC may be for example, $AUC_{0-t}$, $AUC_{0-\infty}$, $AUC_{0-t}$ can be for example AUC from time zero to time t, wherein t is the last time point with measurable concentration for individual formulation.

"Therapeutically effective amount" means the amount of the grape seed extract, when administered to the subject, is sufficient to have a beneficial effect with respect to the modulation of oxidative stress, inflammation, and/or impaired insulin sensitivity of the subject. The "therapeutically effective amount" will vary depending on the condition and its severity, and the age, weight, etc. of the subject to be treated.

Dietary supplementation with GSE improves antioxidant status and impaired insulin resistance following oxidative stress induced by consumption of a high fat meal in human subjects diagnosed with Met.S. In particular, consuming a diet high in readily available carbohydrate/fat increased postprandial oxidative stress and decreased insulin response and the inclusion of GSE in the diet of the subject restored the insulin action possibly by reducing the oxidative stress in human subjects with Met.S. Met.S is one of the major risk factors for cardiovascular disease (CVD). Oxidative stress, inflammation and insulin resistance are common features associated with CVD.

GSE is a polyphenolic-rich extract, rich in mono-, oligo-, and poly-meric polyphenols, with a unique profile of complex polymers and simple phenolic compounds. The active compounds in vivo, may not be the native compounds found in the extract. They are more likely to be metabolites derived from the native compound. Polyphenolic compounds are extensively conjugated in the body, and non-conjugated metabolites most often account for only a minor fraction of the circulating metabolites. This is particularly evident in the case of grape derived products which are monomeric and are often altered during absorption by gut microbiota. Thus bioavailability may be underestimated due to poor detection and identification of metabolites. As described in Sivaprakasapillai et al. (Sivaprakasapillai B., Edirisinghe I., Randolph J., Steinberg F., and Kappagoda T., Metabolism (2009); 58(12), pp 1743-1746) catechins, a compound in GSE, are absorbed into the blood and maximum plasma concentrations ($C_{max}$) were observed at 90-120 min after ingestion.

Postprandial oxidative stress resulting from consumption of a meal that is high in glucose and fat has been suggested as a major factor in the pathogenesis of atherosclerosis and other chronic disease states of diabetes and obesity. This is consistent with the observation that consumption of a meal that is high in readily available carbohydrates and fat results in a postprandial increase in markers of oxidative stress and insulin resistance is consistent with this view (See, Burton-Freeman et al. I, Burton-Freeman et al. II, and Edirisinghe et al.). Furthermore, peak plasma glucose and triglycerides concentrations were observed at 30 and 180 min, respectively after meals.

In one embodiment of the methods provided herein, GSE was administered 60 min before the meal, in order to have significant amount of GSE compounds/metabolites in the blood at the time of peak plasma glucose in the subjects. GSE can also be administered at 5 min to 180 min, preferably 30 min to 120 min, more preferably 60 min to 120 min, even more preferably 60 min to 90 min, before consumption of a meal by a subject. In such method as provided herein using GSE oxidative stress associated with a single high fat meal in people with the MetS is modulated. Without being bound by theory, such responses may be associated with decreased postprandial glucose concentrations and an unchanged plasma insulin profile.

Oxidative stress is thought to play a role in the pathogenesis of glycemic control and disorders of lipid metabolism that are precursors for cardiovascular diseases. Polyphenolic compounds derived from plant foods are believed to exert their beneficial effects in preventing these diseases through their antioxidant activities but the precise mechanisms underlying these effects remain undefined. In the methods described herein, administration of GSE results in an increase in postprandial anti-oxidant activity in the plasma (as defined by the ORAC value in both lipophilic and hydrophilic fractions) and a corresponding reduction in Oxidized LDL concentrations. In a study reported by Leighton et al. (Leighton F, Cuevas O., Guasch V, Perez D. D., Strobel P., San Martin A., Urzua U., Diez M S., Foncea R., Castillo O., Mizon C., Espinoza M A., Urquiaga I., Rozowski J., Maiz A., and Germain A., Drugs Exp. Clin. Res. (1999); 25(2-3), pp 133-141.) it was described that a high fat diet supplemented with red wine significantly increased plasma total antioxidant activity compared to their base line values. Endothelial function, evaluated noninvasively as flow-mediated vascular reactivity of the brachial artery, was also suppressed by a high fat diet. Leighton et al. described that oxidative stress and loss of endothelial function, associated with the high fat diet were normalized after wine supplementation. Several other studies have addressed the potential mechanisms involved in these changes. Serafini et al. (Serafini M, Maiani G, and Ferro-Luzzi A., J Nutr. 1998 June; 128(6): 1003-7) described that the ingestion of alcohol-free red wine may cause significant increases in plasma total radical-trapping antioxidant parameter (TRAP) values and polyphenol concentrations 50 min after ingestion. Neri et al. (Neri S, Signorelli S S, Torrisi B, Pulvirenti D, Mauceri B, Abate G, Ignaccolo L, Bordonaro F, Cilio D, Calvagno S, Leotta C., Clin Ther. 2005 November; 27(11):1764-73) described changes in oxidation-reduction balance, NO bioavailability, and nonthrombogenic endothelial factors after a moderate-fat meal in patients with type 2 diabetes and those with impaired glucose tolerance (IGT). However, these postprandial changes were reversed in all subjects after 15 days of standard antioxidant supplementation. Further, as described in Sivaprakasapillai et al. an inverse relationship of plasma Ox-LDL concentration compared to their baseline valued in the Met.Sy subjects that consumed 300 mg/d of GSE for 4 weeks. These differences were not observed in placebo group.

Excess caloric intake and reduced physical activity induces a state of insulin resistance. When beta cells are no longer able to compensate for insulin resistance by adequately increasing insulin production, impaired glucose tolerance appears, characterized by excessive postprandial hyperglycemia. If impaired glucose tolerance continues, it may evolve into overt diabetes. Insulin resistance, impaired glucose tolerance, and diabetes are major factors for the development of cardiovascular disease. All these conditions are also accompanied by the presence of an oxidative stress, and oxidative stress may be a mechanism in the development of insulin resistance. In the method of modulating oxidative stress, inflammation, impaired insulin sensitivity, or a combination thereof described herein, a significantly reduced postprandial glucose response can be achieved in subjects that consumed GSE compared to the placebo group. However, the postprandial insulin levels remain unchanged between GSE and placebo groups. The method described herein using GSE administered to a subject prior to consumption of a meal improves insulin efficiency.

Insulin signaling is impaired under conditions of oxidative stress and polyphenols have been shown to reverse oxidative stress-induced impairments in insulin signaling. Without being bound by theory, in the methods described herein the effects of GSE on decreased plasma glucose may mediated through improved insulin economy, possibly through modulation of cellular redox status improving insulin signaling. Oxidative stress may increase serine (Ser-307) phosphorylation in Insulin Receptor Substrate I (IRS-I) protein molecules. Serine phosphorylation in IRS-I has been described to possibly inhibit insulin-mediated downstream signaling resulting in impaired glucose uptake. As such, in-vitro studies reported in Sandhya et al. describe that treatment of skeletal muscle cells with a strawberry extract under oxidative stress conditions may decrease IRS-I, Ser-307 phosphorylation and increase IRS-I, Tyr phosphorylation, the stimulatory mechanism for insulin-mediated downstream signaling (See, Sandhya K. et al. (Sandhya K, Tadapaneni R, Banaszewski K, Cappozzo J, Edirisinghe I, Burton-Freeman B., The FASEB Journal 2010; 24:541.13). In overweight men and women, consumption of a strawberry beverage with a high carbohydrate-moderate fat meal significantly reduced the postprandial insulin response compared to when the meal was consumed with a placebo beverage, while the glucose response did not differ between treatments (See Edirisinghe et al.). Moreover, Stull et al., 2010 described increased insulin sensitivity in obese, non-diabetic, and insulinresistant subjects after 8 weeks blueberry supplementation using the hyperinsulinemic euglycemic clamp procedure (Stull A J, Cash K C, Johnson W D, Champagne C M, Cefalu W T. J Nutr. United States, 2010: 1764-8), and Brasnyo et al. described that resveratrol, a stilbene polyphenol found in red wine, improved insulin sensitivity in human subjects with type II diabetes (Brasnyo P, Molnar G A, Mohas M et al. Br J Nutr. England, 2011:383-9). Using the methods described herein using the GSE as described provides that administration of GSE prior to the consumption of a meal improves insulin resistance.

Consumption of high-fat diets can lead to postprandial dyslipidemia resulting in activation of immune cells and changes in gene expression profiles of immune cells. However, in the methods described herein, postprandial inflammatory markers as assessed by plasma IL-6 and TNF-levels are not affected in response to GSE consumption. Perez-Herrera et al. describe that polyphenols may inhibit the inflammatory response through inhibiting the nuclear factor-kappaB (NF-kB) pathways (Perez-Herrera A, et al., Mol Nutr Food Res. 2011 Dec. 9. doi:10.1002/mnfr.201100533. [Epub ahead of print] PubMed PMID:22162245). Further, in Blanco-Colio et al. (Blanco-Colio L. M., Valederrama M., and Alvarez-Sala L. A., Circulation 2000; 102: pp 1020-1026) described that after a fat-enriched meal, NF-kB activation in peripheral blood mononuclear cells (PBMCs) was maximally stimulated at 360 min and remained stimulated through 540 min; whereas red wine consumption with the meal prevented NF-kB activation at 360 and 540 min, an effect not observed with an alternative alcohol (vodka) drink.

As such, in one embodiment, the present invention provides a method of modulating oxidative stress, inflammation, impaired insulin sensitivity or a combination thereof in a subject, comprising administering to the subject a therapeutically effective amount of a grape seed extract. Preferably, the subject is a patient suffering from Metabolic Syndrome (MetS). In particular, the method of the present invention modulates oxidative stress, inflammation, impaired insulin sensitivity, or a combination thereof in a subject suffering from MetS after consuming a meal with moderate to high amounts of readily available carbohydrate and/or fat. Preferably, the oxidative stress, inflammation, or impaired insulin sensitivity in the subject is induced by consumption of a pro-oxidative high carbohydrate, moderate fat meal by the subject. The level of oxidative stress, inflammation, or impaired insulin sensitivity may be even higher in a subject after consuming a high fat content meal, which effects the invention provided herein, reduces or ameliorates.

The method provided herein is advantageous to patients with Metabolic Syndrome (MetS) in its postprandial effect on insulin sensitivity and glucose reduction, but is also advantageous in preventing and/or treating type II diabetes in subjects suffering from MetS in pre-diabetic condition. As such in another embodiment of the present invention there is provided a method of treating a subject suffering from Metabolic Syndrome comprising administering to the subject a therapeutically effective amount of a grape seed extract. Such method can be used in treating postprandial oxidative stress, inflammation, impaired insulin sensitivity or a combination thereof in a subject suffering from Metabolic Syndrome, but may also comprise treating or preventing type II diabetes in a subject in a pre-diabetic condition and suffering from Metabolic Syndrome.

The grape seed extract (GSE) is administered to the subject prior to the consumption of a meal by the subject. Preferably, the GSE is administered 5 min to 180 min, more preferably 30 min to 120 min, even more preferably 60 min to 120 min, even more preferably 60 min to 90 min, before consumption of a meal by a subject. The amount of GSE administered is variable considering parameters such as weight of the subject, severity and stage of the disease the subject is suffering from, and the fat and readily available carbohydrate content of the meal the subject is anticipating of consuming. Preferably, for a moderate to high readily available carbohydrate and/or fat content meal the subject is administered prior to its consumption a dose of 100 mg to 1000 mg, preferably a dose of 200 mg to 500 mg, more preferably a dose of 200 mg to 400 mg, even more preferably a dose of 300 mg of the grape seed extract. Preferably the total dose of GSE per day that is administered to a subject is from 100 mg to 1000 mg, more preferably from 200 mg to 500 mg. The dosage of GSE may be provided in the form of capsules, tablets, a powder, in beverages, in foods, as a neutraceutical, in gummies, and as a variety of food items.

The grape seed extract is a polyphenolic extract comprising pro-anthocyanidins and anthocyanidins. A suitable grape seed extract is a polyphenolic extract comprising monomers, dimers, trimers, tetramers, pentamers and may contain other oligomers and polymers. The GSE suitable for use in the method described herein may be prepared according to the extraction method as described in U.S. Pat. No. 6,544,518 ("the '581 patent"), the contents of which are incorporated herein by reference in its entirety. In general, the '581 patent describes a hot water extraction process involving the following steps. In step (1), grape seeds, dry or fresh, may be heated with hot water for a time sufficient to extract most of the polyphenols. Temperatures of 140-212° F. may be employed, preferably 160-212° F., more preferably 180-212° F., yet more preferably 190-212° F., for a period of about 1-6 hours. The time of heating may be varied in relation to the temperature used. Generally, lower temperatures require longer extraction times. In step (2), the crude grape seed-water extract may be separated from spent seeds by draining over metal screens. The extract may then be cooled and treated with any suitable commercially available pectolytic enzyme, such as Pectinex® Ultra SP-L manufactured by Novo Nordisk, at a concentration of about 50-200 ppm to break down cell wall constituents. Preferably, the seed water extract may be enzyme-treated for a period of two hours at a temperature of 80-120° F. Alternatively, the seed-water extract may be enzyme-treated for 7-14 days or longer at about 40-50° F. In step (3), the resulting turbid seed extract may be acidified with an acid, preferably a mineral acid, more preferably with sulfuric acid, to a pH of approximately 1.5-2.5 and allowed to react from about one hour to about two days. The acidified extract may be cooled for up to several weeks to allow for macromolecules, including proteins and other polysaccharides, to settle. The cooled acidified extract may then be filtered using diatomaceous earth to yield a clarified seed extract. Other filter aids, such as perlite, may also be used.

The grape seed extracts suitable for use in the methods described herein are polyphenolic extracts containing gallic acid of which some or all may be in the form of galloylated epicatechin. An example of such a galloylated tetramer is shown in the following structure:

Such grape seed extract preferably has a total phenol content of between 75-90%, by weight as determined by the method described by Folin Chicalteau, Am J. Enol. Vitic. 1965, 43, 27-43. Preferably, the GSE as a polyphenolic extract comprises 4-11% monomers, 4-9% diamers, 2-4% trimers, 1-4% tetramers, and 1% or less of pentamers all expressed as % by weight as epicatechin equivalents. More preferably the amount of monomers in the polyphenolic extract is from 4-10%, more preferably from 5-9%, even more preferably from 5-8% expressed as % by weight as epicatechin equivalents. More preferably, the amount of diamers in the polyphenolic extract is from 4-8%, even more preferably from 5-7% expressed as % by weight as epicatechin equivalents. The amount of trimers in the polyphenolic extract is from 2-4%, or 2-3% expressed as % by weight as epicatechin equivalents. The amount of tetramer in the polyphenolic extract is from 1-4%, or 1-3% expressed as % by weight as epicatechin equivalents. The amount of pentamers in the polyphenolic extract is 1% or less, or 0.5% or less expressed as % by weight as epicatechin equivalents.

Particularly, the grape seed extract comprises 5 wt % or more epicatechin gallate terminal units. Preferably, a suitable grape seed extract for use in the methods described herein comprises 8-9 wt % epicatechin gallate units. More preferably such suitable grape seed extract comprises 12 wt % or more of epicatechin terminal units. A grape seed extract useful in the methods described herein contains gallic acid either as free gallic acid or galloylated to epicatechin or both. Preferably, the total amount of free gallic acid in such grape seed extract is from 0-2% by weight measured by HPLC. More specifically, a suitable grape seed extract comprises catechin, epicatechin and gallic acid and also comprises dimer B, a proanthocyanidin dimer having several isomers all of which are included in the term dimer B, and/or a polymer. In a specific embodiment the grape seed extract comprises 5.7% total gallic acid (both free and bound (galloylated)), 6.7% catechin, 4.8% epicatechin, 34.4% dimer B, and 46.1% polymers.

In another embodiment, the present invention provides a pharmaceutical composition comprising a grape seed extract and a pharmaceutical acceptable excipient for modulating post-prandial oxidative stress, inflammation, impaired insulin sensitivity, or a combination thereof in a subject suffering from Metabolic Syndrome.

In another embodiment of the present invention there is provided a use of a composition comprising grape seed extract (GSE) for modulating oxidative stress, inflammation, impaired insulin sensitivity, or a combination thereof in a subject. The subject may be suffering from Metabolic Syndrome (MetS).

Pharmaceutical formulations of the present invention contain the grape seed extract as described herein. In addition to the active ingredient(s), the pharmaceutical formulations of the present invention may contain one or more excipients. Excipients are added to the formulation for a variety of purposes.

Diluents may be added to the formulations of a present invention. Diluents increase the bulk of a solid pharmaceutical composition, and may make a pharmaceutical dosage for containing the composition easier for the patient and caregiver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate, dehydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into dosage form, such as a tablet, may include excipients whose functions include helping to bind the active ingredient and other excipients together after compression. Binders for solid pharmaceutical compositions include *acacia*, alginic acid, carbomer (e.g., carbopol), carboxymethylcellulose sodium, dextrin, ethyl cellulose, gelatine, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminium silicate, maltodextrin, methylcellulose, polymethacrylates, povidone (e.g., KOLLIDON® PALSDONE®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELOSE®), colloidal silicon dioxide, croscarmellose sodium, crospovidone (e.g., KOLLIDON®, POLYPLASDONE®), guar gum, magnesium aluminium silicate, methyl cellulose, microcrystalline cellulose, polacrilin potassium, powdered cellulose, pregelatinized starch, sodium alginate, sodium starch glycolate (e.g., EXPLOTAB®), and starch.

Glidants can be added to improve the flowability of a non-compacted solid composition, and to improve the accuracy of dosing. Excipients that may function as glidants include colloidal silicon dioxide, magnesium trisilicate, powdered cellulose, starch, talc, and tribasic calcium phosphate.

When a dosage form such as tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion, and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavour enhancers make the dosage form more palatable to the patient. Common flavoring agents and flavour enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance, and/or facilitate patient identification of the product and unit dosage level.

In liquid pharmaceutical compositions prepared using grape seed extract, the grape seed extract and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in liquid carrier. Emulsifying agents that may be useful in liquid compositions of the present invention include, for example, gelatin, egg yolk, casein, cholesterol, *acacia*, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include *acacia*, alginic acid bentonite, carbomer, carboxymethylcellulose calcium or sodium, cetostearyl alcohol, methyl cellulose, ethylcellulose, gelatine guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xantham gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated, hydroxyanisole, and ethylenediamine tetraacetic acid may be added at levels safe for ingestion to improve storage stability.

A liquid composition may also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant, and ophthalmic, administration. Although the most suitable administration in any given case will depend on the nature and severity of the condition being treated, the most preferred route of the present invention is oral.

Dosage forms include solid dosage forms like tablets, powders, capsules, suppositories, sachets, troches, and lozenges, as well as liquid syrups, suspensions, elixirs, and in beverages.

The dosage form of the present invention may be a capsule containing the composition, preferably a powdered or granulated solid composition of the invention, within either a hard or soft shell. The shell may be made from gelatin, and, optionally, contain a plasticizer such as glycerine and sorbitol, and an opacifying agent or colorant.

A composition for tableting or capsule filling may be prepared by wet granulation. In wet granulation, some or all of the active ingredients and excipients in powder form are blended, and then further mixed in the presence of a liquid, typically water, that causes the powders to clump into granules. The granulate is screened and/or milled, dried, and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet, and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules.

Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The active ingredient and excipients may be formulated into compositions and dosage forms according to methods know in the art.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Human Clinical Trial

The Human Subjects Research Committee of the University of California, Davis, approved the study. All participants signed a written informed consent form before any study-related procedures were performed; verbal consent was given during the telephone interview prior to answering study screening questions.

Grape Seed Extract

The GSE (GSE, MegaNatural®-Gold)) used in the study was obtained from Polyphenolic Inc, Madera, Calif. Total phenolic level is 94.3 gallic acid equivalents (wt/wt) as assessed by the Folin & Ciocalteu method. The moisture content is 4.1%. The detailed polyphenolic composition as assessed using LC-MS/MS is given in Table 1.

TABLE 1

| Polyphenolic composition of the Grape Seed Extract (GSE) * ||
|---|---|
| Name of the compound | % composition |
| Total Gallic Acid | 5.7 |
| Catechin | 6.7 |
| Epicatechin | 4.8 |
| Dimer B | 34.4 |
| Polymer | 46.1 |

* Meganatural Gold, Polyphenolic, Inc, Madera, CA

Subjects

Twelve subjects (n=12, 7 females and 5 males) identified with Met S according to the NCEP III guidelines (1) were recruited through newspapers, posters, and direct contact in the Davis and Sacramento area of northern California. All 12 subjects completed the study. Eligible subjects were required to be non-smokers and in generally good health. Individuals with clinical evidence and/or history of cardiovascular, respiratory, renal, gastrointestinal, metabolic or hepatic disease/conditions, who used prescription and/or over the counter medications that may interfere with study endpoints (i.e. antioxidant supplements, anti-inflammatory drugs, lipid lowering medications), had unusual dietary habits (e.g., pica), were actively losing weight or addicted to drugs and/or alcohol were not eligible for participation.

The age and BMI of the subjects were 45±15 y and 36±7 kg/m$^2$, respectively (Mean±standard deviation (SD). A baseline metabolic panel is listed in Table 2.

TABLE 2

| Baseline Characteristics of study subjects (n = 12) ||
|---|---|
| Male/Female | 5/7 |
| BMI | 35.9 ± 6.7 |
| Age (Y) | 45 ± 15 |
| Baseline metabolic panel | |
| Glucose (mg/dL) | 104.5 ± 22.8 |
| Insulin (µIU/mL) | 25.0 ± 7.2 |

TABLE 2-continued

| Baseline Characteristics of study subjects (n = 12) ||
|---|---|
| HOMA -IR | 3.3 ± 1.1 |
| Triglycerides (mg/dL) | 156.0 ± 38.9 |
| Total Cholesterol (mg/dL) | 197.1 ± 56.2 |
| LDL Cholesterol (mg/dL) | 122.6 ± 45.6 |
| HDL Cholesterol (mg/dL) | 43.7 ± 11.6 |
| Systolic Blood Pressure (mmHg) | 132.5 ± 11.0 |
| Diastolic Blood Pressure (mmHg) | 78.7 ± 8.8 |

Study Design and Treatments

This study was a single-center, randomized, cross-over, 2-arm, placebo-controlled, 360-min postprandial trial conducted at the University of California Davis Clinical and Translational Science Center (CTSC) Clinical Research Center (CCRC) at the UC Davis Medical Center-affiliated Northern CA Veteran's Affairs (VA) Medical Center in Mather, Calif. Enrolled participants were required to limit polyphenolic containing foods/food product consumption throughout the study period starting 1 week prior to the first study visit; all other aspects of diet and physical activity remained constant. Subjects were randomized to receive one of the two capsules (GSE or Placebo) along with a high fat breakfast meal in a randomly selected sequence. Each subject received both of the treatments (~1 week apart) and served as his/her own control. The high fat breakfast meal was prepared to provide approximately 670 kcal with ~40% of energy from fat (Table 3). Test meals were prepared in the metabolic kitchen at the CTSC with strict adherence to food and safety standards.

TABLE 3

| Composition of the Test meals * ||
|---|---|
| Bagel[#] | 110 g |
| Cream cheese | 14 g |
| Margarine[$] | 5 g |
| Egg | 50 g |
| Canteloupe | 85 g (7-8 chunks) |
| Whole Milk | 240 ml |
| Calorie content | ~670 kcal |
| Calories derived from fat | 40% |

* All ingredients were purchased from local super market.
Bagel[#] was toasted.
Margarine[$] was used to scramble the egg.

Postprandial Testing Protocol

All procedures were identical during both study visits with the exception of the capsule (GSE or Placebo) consumed. Postprandial testing was conducted according to standardized protocols previously developed (See Burton-Freeman et al. I, Burton-Freeman et al. II, and Edirisinghe et al.). Subjects arrived at the CTSC in the morning after an overnight fast on two separate occasions; study visits were between 7 and 10 days apart. On study visit mornings, a Registered Nurse (RN) placed an indwelling catheter in the antecubital vein of the non-dominant arm of subjects. Immediately following the initial blood draw (Time=−1), subjects were orally administered a GSE or Placebo capsule with water. At 1 hour later (Time=0), a blood sample was drawn and the subjects ate a high fat meal of common breakfast foods; the meal was consumed within 20 minutes. Blood was collected hourly thereafter to 6 hours, timed from the consumption of the capsule. Blood was processed for subsequent laboratory analysis including: plasma lipids, glucose, insulin, oxidized LDL (OxLDL), interleukin 6 (IL-6) and tumor necrosis factor-alpha (TNF-α). Three day food records (1 set per week) were maintained and reviewed by a dietitian with subjects for compliance to limited polyphenolic intake throughout the study period.

Analytical Methods

Various analytical methods were deployed to assess the effect of GSE consumption on fasting and postprandial concentrations of plasma lipids, glucose, insulin, OxLDL, hsCRP, IL-6 and TNF-α. Lipids and glucose were measured using standardized enzyme-based assay kits (Randox, Antrim, UK) on the Randox Daytona Auto Clinical Analyzer (Oceanside, Calif.). Insulin was measured using the AlphaLISA method (Perkin Elmer, Waltham, Mass.). Measurement of OxLDL was determined by ELISA assay kits (Mercodia Inc., Winston Salem, N.C.) and measurement of IL-6, and TNF-α were measured by highly-sensitive ELISA assays (R&D Systems, Minneapolis, Minn.). All assay protocols were performed according to the manufacturers' instructions and appropriate quality controls were used as applicable.

Oxygen radical absorbance capacity (ORAC) assay is performed according the method described by Prior et al. (Prior R L, Gu L, Wu X, Jacob R A, Sotoudeh G, Kader A A, Cook R A., J Am Coll Nutr. 2007 April; 26(2):170-81.) with some modifications. Plasma ORAC values were obtained for hydrophilic and lipophilic fractions separately. Plasma (100 µL) was transferred to a glass tube, 200 µL of ethanol (specifications) and 100 µL of distilled water is added and mixed, and then 400 µL of hexane (specifications) is added, followed by mixing. The mixture was left to sit for until two layers appeared (~2 min) and centrifuged for 5 min at 14 000 rpm (centrifuge and the rotor). The upper hexane layer was removed and added to a separate amber glass tube. An additional 400 µL of hexane was added to the original tube, mixed, and centrifuges as above. The hexane layer was removed again and combined with the first extract. The combined hexane extracts were dried down under a stream of nitrogen flow in preparation for lipophilic ORAC analysis. Any hexane remaining following hexane extraction of the aqueous plasma sample was removed by drying under nitrogen flow. Protein in the samples was precipitated using 600 µL of 0.5 mol/L perchloric acid and centrifuged for 5 min at 14 000 rpm (Centrifuged and the rotor). Supernatant (100 µL) was removed and mixed with 900 µL of phosphate buffer saline (PBS). This fraction was used to determine the ORAC values of hydrophilic fraction.

Sample from hydrophilic and lipophilic fractions (25 µL) was added to a well in a 96 well micro-plate (specifications) and the mixed with 150 µL of fluorescein solution 25 µL of AAPH. Florescent decay reading was initiated immediately. A Perkin Elmer Envision plate reader (Perkin Elmer, Waltham, Mass., USA) was used to measure the fluorescent decay at a 60 s interval for 60 min at an excitation/emission wavelength of 485 nm/528 nm. A standard curve was obtained by plotting Trolox concentrations against the corresponding area under the curve for each standard. ORAC values for the unknown samples were calculated using the standard curve.

Statistical Analysis

Postprandial changes in glucose, triglycerides, cholesterol, insulin and ORAC in response to GSE or placebo with high fat meals were compared as area under the curve over 6 h periods. Furthermore, Ox-LDL and inflammatory markers were analyzed by repeated measures analysis of variance RM-ANOVA using PC-SAS (version 9.1.3; SAS Institute Inc, Cary, N.C.) GLM and MIXED procedure with treatment, time, as main factors and subject as the blocking variable. The postprandial responses with the two treatments (GSE and Placebo) were compared in terms of the least squares mean (LSM) as an estimate of the 360 min (6 h) response. Treatment associated difference were also evaluated in terms of changes in time relative to baseline and at common time points between treatments. The level used to determine statistical significance was $p<0.05$.

Postprandial Responses

Figure 1A:
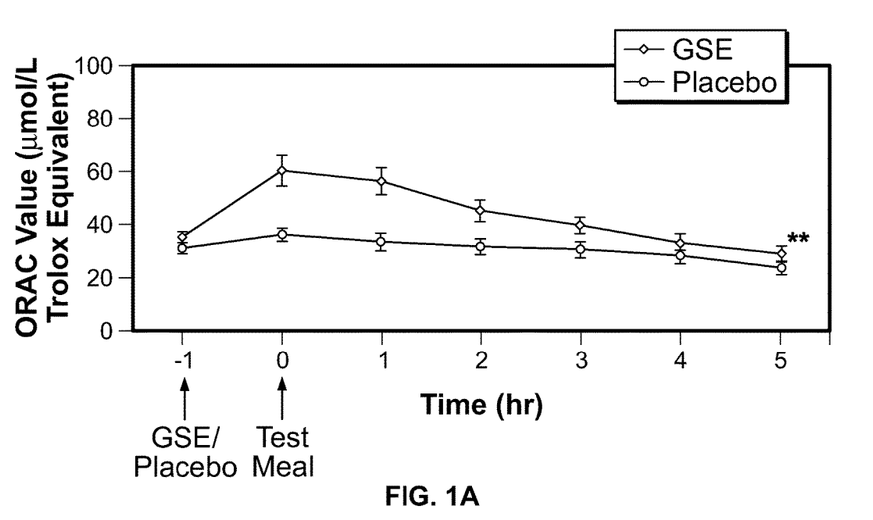
Figure 1B:
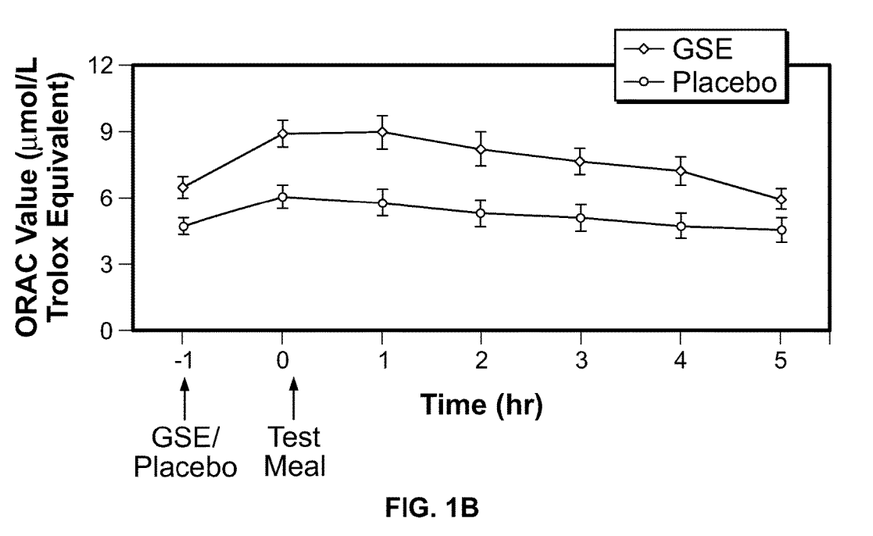

Oxidative stress markers were assessed using plasma and plasma ORAC (hydrophilic and lipophilic) and OxLDL assays. Plasma ORAC values were assessed in hydrophilic and lipophilic fractions separately (FIGS. 1A and B). Peak plasma hydrophilic and lipophilic ORAC values were observed at 1 hr after the meal in both GSE and placebo treated groups, and were significantly different compared to their respective baseline values (−1 hr, $P<0.05$). The plasma hydrophilic and lipophilic ORAC values at baseline (−1 hr) and 5 hr after the meal were not significantly different in response to GSE or placebo treatments ($P>0.05$). Analysis of the positive incremental AUC response (−1 to 5 hr) revealed significantly increased hydrophilic ORAC values with GSE groups compared to placebo (GSE—hydrophilic positive incremental AUC 3064.3±570.3 vs. positive incremental AUC Placebo 1034.7±462.6 J/mol·hr/L Trolox equivalents, $P<0.05$). However, analysis of the positive incremental AUC response in lipophilic ORAC values were not significantly different in GSE vs Placebo group ($P>0.05$).

Changes in glucose, lipids, insulin and biomarkers of oxidative stress and inflammation were measured over the 6 hr experimental period at defined intervals after capsule consumption. Responses after the GSE and placebo along with test meals were compared as total AUC or positive incremental AUC from −1 hr to 5 hr. Total AUC for triglyceride and cholesterol responses were not significantly different between groups ($P>0.05$, data not shown).

Figure 2:
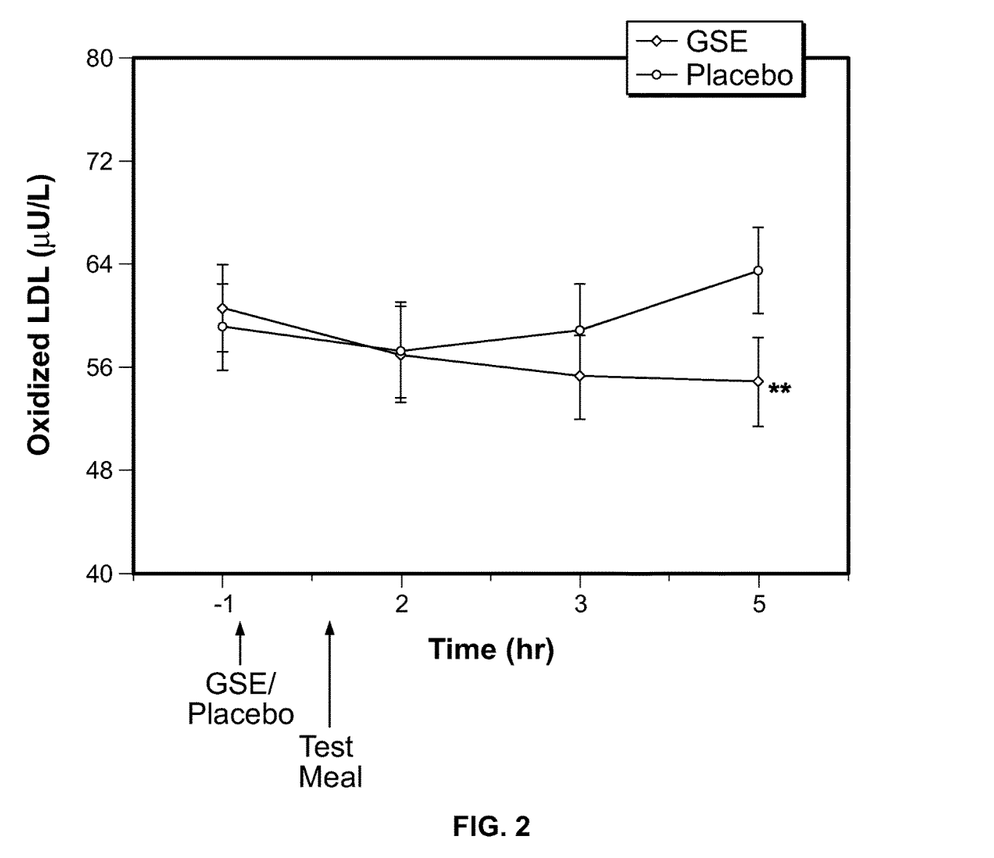
Figure 3A:
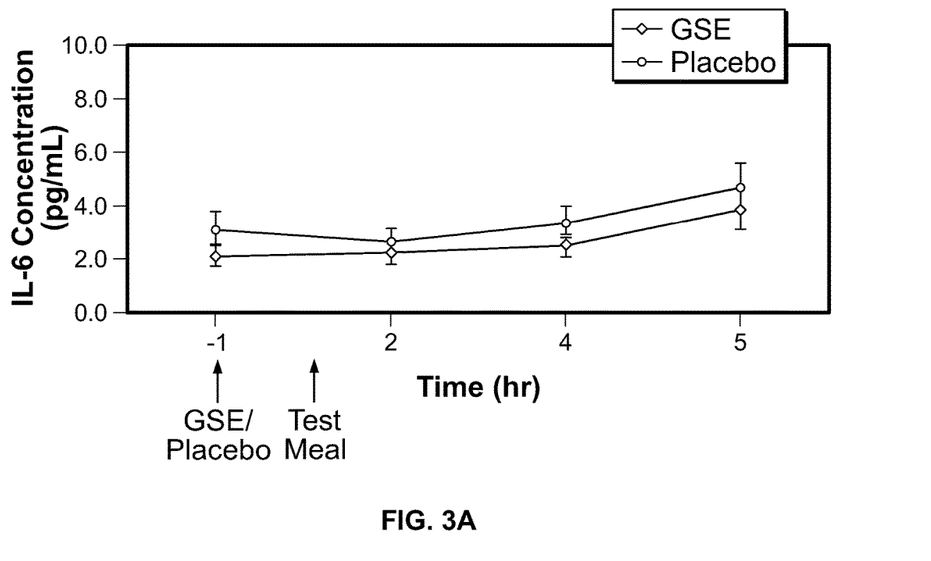
Figure 3B:
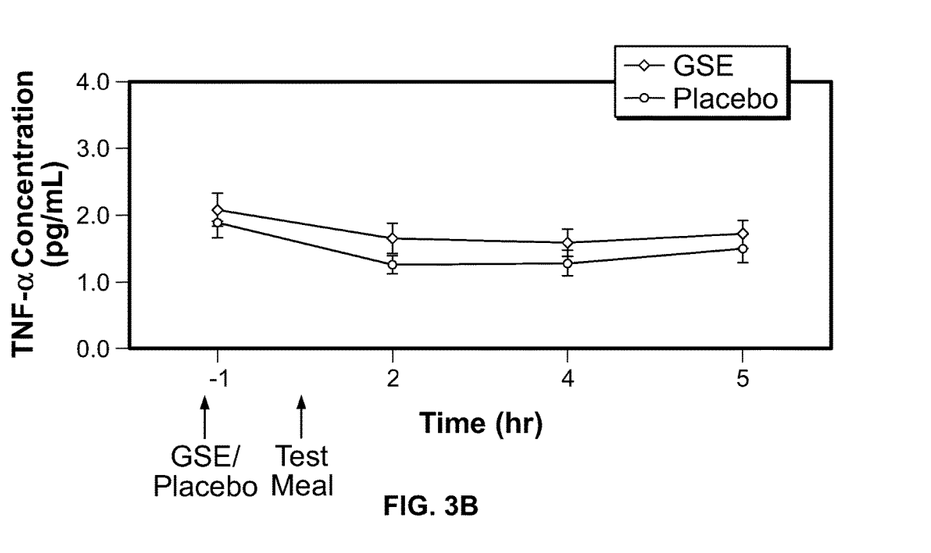

Postprandial OxLDL concentrations were significantly increased at 5 hr after the breakfast meal compared to fasting values (−1 hr) in the placebo group ($P<0.05$), whereas in the GSE group, OxLDL concentrations were significantly reduced at 5 hr after the breakfast meal compared to fasting concentrations (−1 hr) (FIG. 2). Significant changes were not observed with IL-6 and TNF-α between GSE and placebo groups (FIGS. 3A and B).

Figure 4:
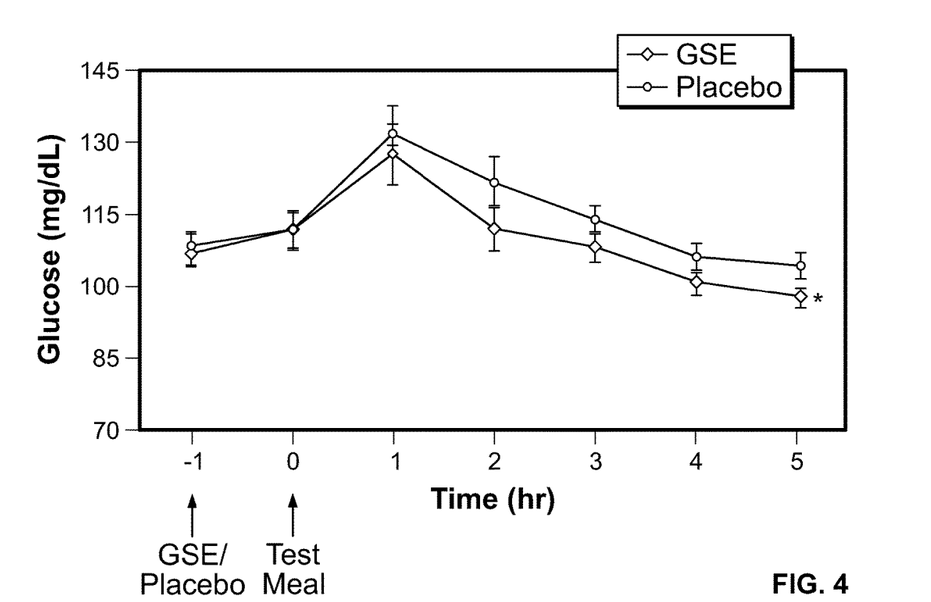
Figure 5:
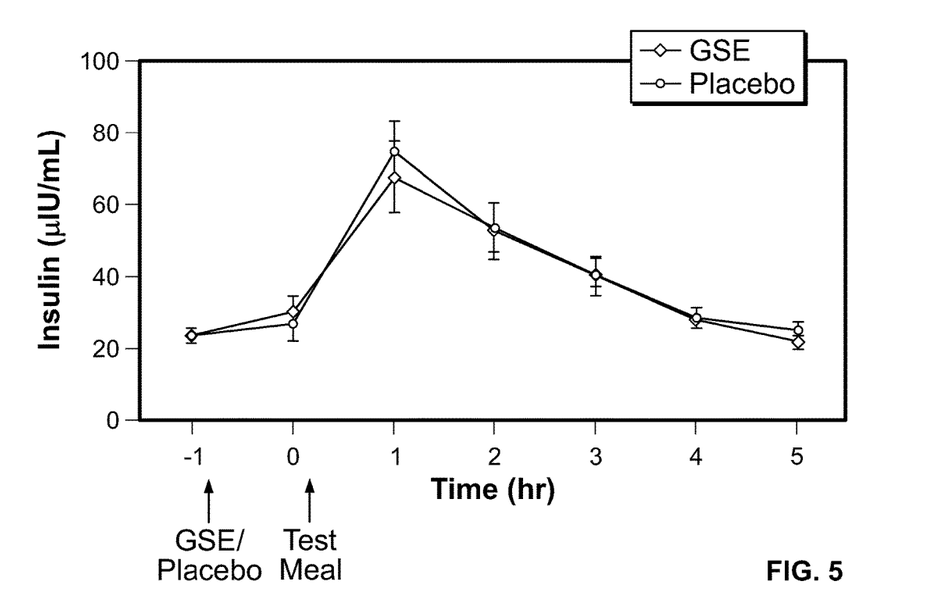

The postprandial glucose response after consumption of the meal preceded by the placebo or GSE capsule (at −1 hr) is shown in FIG. 4. Between −1 hr and 0 hr (just before meal consumption), glucose concentrations did not significantly differ ($P>0.05$). After the meal glucose concentrations peaked at approximately 1 hr after both treatments and the values at 1 hr did not significantly differ between two groups ($P>0.05$). Analysis of total AUC revealed significantly lower glucose over the 6 hr experimental period with GSE compared to placebo (GSE total AUC 667.4±63.6 vs. total AUC placebo 691.0±59.1 mg/dL*hr, $P<0.05$). Peak plasma insulin concentrations were also observed at approximately 1 hr after meal consumption for both treatments. The insulin responses in the GSE treated group compared to the placebo group were not significantly different (Total GSE AUC 251.7±96.2 vs. placebo 262.8±82 µIU/L*hr, P>0.05, FIG. 5).

What is claimed is:

1. A method of treating inflammation, impaired insulin sensitivity or a combination thereof in a subject, comprising administering to the subject a therapeutically effective amount of a grape seed extract, wherein the grape seed extract is a polyphenolic extract comprising
    4-11% monomers,
    4-9% dimers,
    2-4% trimers,
    1-4% tetramers,
    0.5% or less of pentamers expressed as % by weight as epicatechin equivalents, and having a epicatechin gallate terminal unit content of 5 wt % or more.

2. The method according to claim 1, wherein the grape seed extract has 0-2 wt % of free gallic acid.

3. The method according to claim 1, wherein the grape seed extract comprises 12 wt % or more epicatechin gallate units.

4. The method according to claim 1, wherein the grape seed extract comprises 5.7% total gallic acid, 6.7% catechin, 4.8% epicatechin, 34.4% dimer B, and 46.1% polymer.

5. The method according to claim 1, wherein the grape seed extract comprises 12 wt % or more of epicatechin terminal units.

6. The method according to claim 1, wherein the grape seed extract comprises 8 to 9 wt % of epicatechin gallate units.

7. The method of claim 1, wherein the grape seed extract is a polyphenolic extract comprising 4-10% monomers, 4-8% dimers, 2-3% trimers, 1-3% tetramers, and 0.5% or less of pentamers expressed as % by weight as epicatechin equivalents, and having a epicatechin gallate terminal unit content of 5 wt % or more.

8. The method of claim 7, wherein the content of monomers in the grape seed extract is 5-9 weight %.

9. The method of claim 8, wherein the content of monomers in the grape seed extract is 5-8 weight %.

10. The method of claim 9, wherein the content of dimers in the grape seed extract is 5-7 weight %.

11. The method of claim 7, wherein the content of dimers in the grape seed extract is 5-7 weight %.

12. The method of claim 8, wherein the content of dimers in the grape seed extract is 5-7 weight %.

* * * * *